(12) United States Patent
Alfonso

(10) Patent No.: US 9,572,959 B2
(45) Date of Patent: Feb. 21, 2017

(54) USER WEARABLE DEVICE FOR CARRYING PERITONEAL DIALYSIS CATHETER

(71) Applicant: Edward Alfonso, Riverside, CA (US)

(72) Inventor: Edward Alfonso, Riverside, CA (US)

( * ) Notice: Subject to any disclaimer, the term of this patent is extended or adjusted under 35 U.S.C. 154(b) by 0 days.

(21) Appl. No.: 14/515,237

(22) Filed: Oct. 15, 2014

(65) Prior Publication Data

US 2015/0105730 A1    Apr. 16, 2015

Related U.S. Application Data

(63) Continuation-in-part of application No. 12/400,506, filed on Mar. 9, 2009, now abandoned.

(51) Int. Cl.
*A61M 25/02* (2006.01)
*A61M 1/28* (2006.01)

(52) U.S. Cl.
CPC ............. *A61M 25/02* (2013.01); *A61M 1/285* (2013.01); *A61M 2025/024* (2013.01); *A61M 2025/0206* (2013.01); *A61M 2025/028* (2013.01)

(58) Field of Classification Search
CPC .................. A61M 25/02; A61M 1/285; A61M 2025/0206; A61M 2025/024; A61M 2025/028
See application file for complete search history.

(56) References Cited

U.S. PATENT DOCUMENTS

| | | | |
|---|---|---|---|
| 4,570,898 A | 2/1986 | Staeubli | |
| 4,578,062 A | 3/1986 | Schneider | |
| 4,707,906 A | 11/1987 | Posey | |
| 4,973,314 A | 11/1990 | Garnett | |
| 5,222,486 A * | 6/1993 | Vaughn | A61M 16/08 128/200.24 |
| 5,297,546 A | 3/1994 | Spofford et al. | |
| 5,496,282 A * | 3/1996 | Militzer | A61M 25/02 128/DIG. 26 |
| 5,549,645 A * | 8/1996 | Frey | A61M 1/285 604/174 |
| 5,688,248 A | 11/1997 | Lessing, Jr. | |
| 6,027,489 A | 2/2000 | Galato | |
| 6,126,639 A | 10/2000 | Sutherland et al. | |
| 6,206,854 B1 | 3/2001 | Weaver | |
| 6,436,074 B1 | 8/2002 | Lee | |
| 6,579,268 B1 | 6/2003 | Loining | |
| 6,682,507 B2 | 1/2004 | Irish | |

\* cited by examiner

*Primary Examiner* — Emily Schmidt
*Assistant Examiner* — Lauren M Peng
(74) *Attorney, Agent, or Firm* — Kirk A. Buhler; Buhler & Associates

(57) ABSTRACT

Improvements in an easily wearable catheter. A housing secures the components of the catheter, i.e. the valve, the removable cap, the twist valve, and the hose, to the user by means of an attachment. The present retainer for a peritoneal dialysis catheter relates generally to continuous ambulatory peritoneal dialysis methods and systems and, more particularly, to a user-wearable catheter housing which does not require any tape, belt or other bulky retainer to keep the catheter attached to the user.

14 Claims, 5 Drawing Sheets

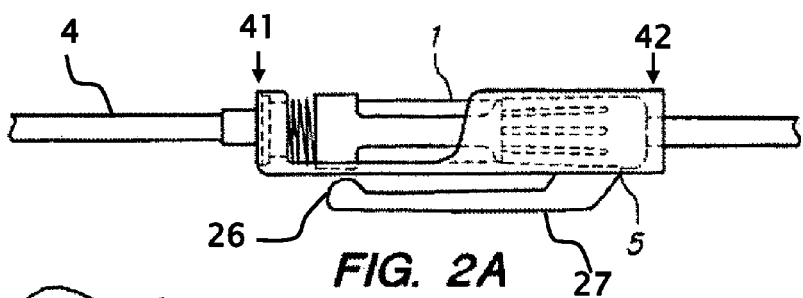
FIG. 2A
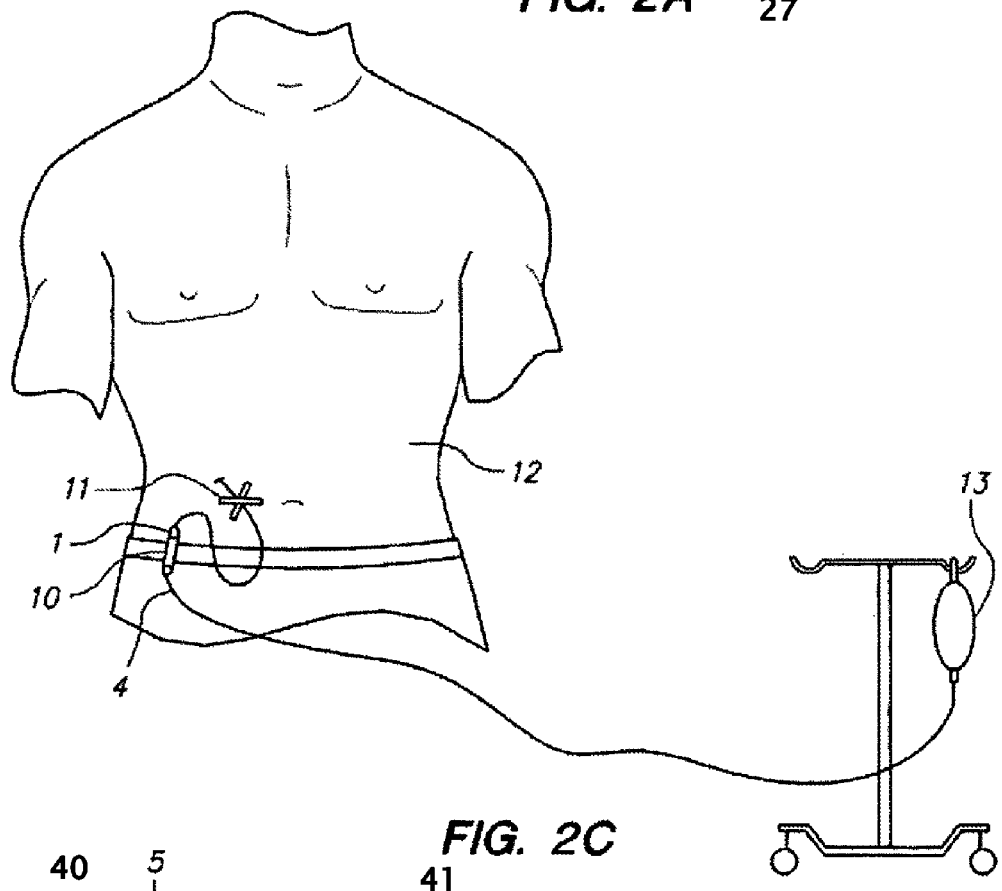
FIG. 2C
FIG. 2B

USER WEARABLE DEVICE FOR CARRYING PERITONEAL DIALYSIS CATHETER

CROSS REFERENCE TO RELATED APPLICATION

This application is a continuation-in-part of applicant's co-pending application Ser. No. 12/400,506 filed Mar. 9, 2009 the entire contents of which is hereby expressly incorporated by reference herein.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

The present invention relates to a housing for the components of a catheter and method for securing the catheter housing to the user or wearer. The field of my invention covers user-wearable catheters for peritoneal dialysis which general consist of a catheter, a removable cap, a twist valve, and a hose. My invention adds a means for holding the components of the catheter together in a single housing unit and providing a means for attaching the catheter housing to the user comfortably and safely.

Description of Related Art Including Information Disclosed Under 37 CFR 1.97 and 1.98

A catheter is a tube that is inserted into the body, thereby allowing drainage or injection of fluids or access by surgical instruments. In most uses the catheter is a thin, flexible, tube extending from the body of the user through an exit site. In existing catheter retainers or housings, either tape or a belt is used to secure the catheter to the body of the user in between dialysis treatments. See FIG. 1.

Peritoneal dialysis replaces the blood cleaning work of the kidneys fig people with kidney failure. A surgeon places a small, soft tube (catheter) into the patient's abdomen during an operation under general anesthesia. The catheter has a free end that extends outside the body of the patient through an exit site. During peritoneal dialysis, a dialysis solution of sugar and minerals is dissolved in water and flows through the catheter into the patient's abdomen by means of gravity from a bag. The high concentration of sugar in the solution draws wastes, chemicals, and extra water from the peritoneal membrane into the solution through osmosis.

After all of the dialysis solution has entered the patient's abdomen, the catheter is disconnected until the next treatment. In between treatments, a sterile cap is placed on the free end of the catheter, and, in the prior art, the catheter device is secured to the patient's body by tape or a belt. In the meantime, the patient must wear the free end of the catheter until the next treatment while avoiding any pulling or excessive movement of the catheter. Up to now, the preferred methods for carrying the free end of the catheter included tape, belts, and pockets. FIG. 1. A major disadvantage of the current methods and devices for holding together and wearing the components of a catheter is that existing tapes, belts, and pockets are clumsy and bulky. Thus, there is a need in the industry for a convenient device to hold the catheter components together in a compact housing and an accompanying method for easily and comfortably wearing the catheter housing.

Each of these prior art methods have significant drawbacks. Using tape is uncomfortable to the user because tape sticks to the skin of the user, thereby making it painful and difficult to adjust or remove the catheter. Before using tape, the skin of the user must be shaved and other uncomfortable preparation steps must be taken. For example, multiple pieces of tape are required to secure the catheter on the body of the wearer, and subsequently these pieces must be removed periodically for cleaning and re-positioning. The resulting skin abrasions and rashes increase the risk of injury and infection for the patient while limiting the user's range of motion, thus making employment and everyday life painful and dangerous.

As the tape becomes dirty and contaminated, the risk of infection rises so that the useful life of tape-systems is limited. Accordingly, there is a need in the industry for a catheter housing that uses no tape and requires no preparation of the user's body such as shaving. An additional need is for a housing unit that holds the catheter in place or around the user with no outside tape or other material which attracts contaminants.

Wearing the tape causes inconvenience whenever the user takes a shower or a bath because the tape must be removed or otherwise made water-proof. The tape must be replaced frequently, up to four times daily, thus requiring significant time to maintain while also causing increases in skin irritation. Accordingly, there is a need in the industry for a Catheter Housing that may be easily worn or kept clean during everyday use. There is an additional need in the industry to for a catheter device, housing, and method that will allow the wearer to engage in everyday activities such as taking a shower.

Another method for securing the free end of the catheter is by means of a belt. Some examples of these belt-based devices include using nylon straps around the waist or cotton netting belts, or pockets to secure the catheter. The belt or pocket retains the catheter while the belt or pocket is wrapped around the waist of the user. In other examples, the catheter-belt is attached to the body of the user. One disadvantage of using belts and pockets is that they are unwieldly, become uncomfortable, and restrict the range of movement of the wearer.

Belts also collect dirt and retain water from the surrounding environment. For example, for a patient using a belt-based catheter during a shower there are significant dangers of sustaining an infection in and around the catheter exit site. What is needed in the industry is a device and means for holding the catheter together in a housing without impacting the exit site. In addition, there is a need in the industry for a light, simple, and flexible catheter housing to retain the catheter's components and connect the catheter to the body of the user without causing discomfort or collecting water and contaminants.

The deficiencies of the prior art for carrying the free-end of the catheter cause significant pain to users whose catheter exit sites become infected. Existing holding devices for the catheter components and existing methods for attaching the catheter housing to the body of the user create substantial dangers danger of internal infection and even death.

Peritonitis is an infection of the peritoneum and abdominal cavity. This disease is a serious complication of peritoneal dialysis that is frequently caused by accidents involving the free end of the catheter. Using belts, tapes, pockets, and similar means for retaining the catheter increases activity near the exit site and creates significant risks for the user. Consequently, there is a need in the industry for an easy to wear device and easy to use method for securing the catheter device in between dialysis treatments. There is also a need in the industry for a device and method for carrying the free end of the catheter and its parts, i.e. the twist valve, the removable cap, and the hose, without the disadvantages of using tapes or the bulkiness of belts or pockets.

Using conventional attachment means in the prior art for securing the catheter to the body of the user is semi-permanent in that it takes much effort to release or de-attach the catheter and its housing. Hence, it is also desirable to develop a catheter retainer that easily secures the catheter and housing to the body of the user but also allows for the easy release of the free end of a catheter. See FIG. 2.

PRIOR ART AND BACKGROUND OF THE INVENTION

U.S. Pat. No. 4,973,314 issued on Mar. 31, 1989 to Susan Garnett, titled Combined Dressing and Retainer For Surgically Implanted Catheter. This patent illustrates the original problems with using tape or gauze for implanted catheters.

U.S. Pat. No. 4,578,062 issued on Mar. 25, 1986 to Paul E. Schneider, titled Intravenous Catheter Housing. Holding the catheter is achieved by means of a belt which is uncomfortable to wear and attracts contamination.

U.S. Pat. No. 5,688,248 issued on Nov. 18, 1997 to Kennith C. Lessing, Jr. titled Adult and Pediatric Peritoneal Dialysis Catheter Belt Pack. U.S. Pat. No. 4,378,062 issued on Mar. 25, 1986 to Paul E. Schneider, titled Intravenous Catheter Housing. Holding of the catheter is achieved by means of a belt which is uncomfortable to wear and attracts contamination.

U.S. Pat. No. 6,027,489 issued on Feb. 22, 2000 to Raffaele Galato, titled Device for the Connection In a Sterile Environment of a Peritoneal Catheter to a Dialysis Liquid Drain or Feed Tube. This device provides for a sterile environment for dialysis but does not address the need for easily housing of all the components of the catheter and subsequent safe wearing by the user.

U.S. Pat. No. 6,126,639 issued on Nov. 19, 1998 to Joanne Sutherland et al., titled "Continuous Ambulatory Peritoneal Dialysis Catheter Support Undergarment." This is an undergarment that the user must wear around his body.

U.S. Pat. No. 6,436,074 issued on Nov. 28, 2000 to Jarrel Lee, titled "Garment For Securing and Exposing a Peritoneal Dialysis Catheter and Catheter Exit Site". This device uses a torso belt, with all the disadvantages discussed above.

U.S. Pat. No. 6,579,268 issued on Oct. 25, 2001 to Michelle Loining, titled "Catheter Support Pouch". This invention is a pouch for releasably securing the free end of a catheter made of cloth or fabric.

U.S. Pat. No. 6,682,507 132 issued on Feb. 20, 2002 to Douglas H. Irish, titled User Wearable Device Having Sterile Environment For Connecting Peritoneal Dialysis Tubes, uses a pouch to facilitate ambulatory dialysis. U.S. Pat. No. 6,579,268 issued on Jun. 17, 2003 to Michelle J. Loining titled Catheter Support Pouch. U.S. Pat. No. 6,206,854 issued on Mar. 27, 2001 to Kathleen M. Weaver titled Catheter Garment. While user wearable, this device is bulky and relies on a belt to attach to the body of the user.

What is needed is a retainer for a retainer for a peritoneal dialysis catheter that seals the end of the catheter and allows the catheter to be easily removed from the retainer. The retainer can remain connected to a ribbon that extends around the neck of the user or the retainer can be clipped to the clothing of a person.

BRIEF SUMMARY OF THE INVENTION

One object of my retainer for a peritoneal dialysis catheter is to reduce the overhead of maintenance. By using simple, non-invasive, and non-contact means of attaching the catheter's housing to the body of the user, my retainer for a peritoneal dialysis catheter incurs no risk of cuts to the skin or the catheter tubes which may require additional surgery.

Another object of my retainer for a peritoneal dialysis catheter is to keep the catheter end free at all times, so that water, dirt, and germs do not accumulate on the exit site or other parts of the user's body. By making my retainer for a peritoneal dialysis catheter so that the catheter itself is free-moving, my retainer for a peritoneal dialysis catheter does not collect water or dirt and thereby eliminates contamination because no bulky belt or pocket is used.

Still another object of the retainer for a peritoneal dialysis catheter for the peritoneal dialysis catheter to be removable retained within the holder. The retention leaves the tube free to pass through the retainer and provides retention of the seal on the catheter to prevent contamination.

Various objects, features, aspects, and advantages of the present invention will become more apparent from the following detailed description of preferred embodiments of the invention, along with the accompanying drawings in which like numerals represent like components.

BRIEF DESCRIPTION OF THE SEVERAL VIEWS OF THE DRAWING(S)

FIG. 1 illustrates the catheter 1 with components, i.e.: the removable cap 2, the middle portion of the catheter valve, the twist valve, and the connected-end and the free-end of the rubber hose.

FIG. 2A shows the catheter 1 and the clip connected 27 to the housing 5.

FIG. 2B shows the catheter 1 on a person 12.

FIG. 2C shows the catheter housing 5.

Figure 3A:
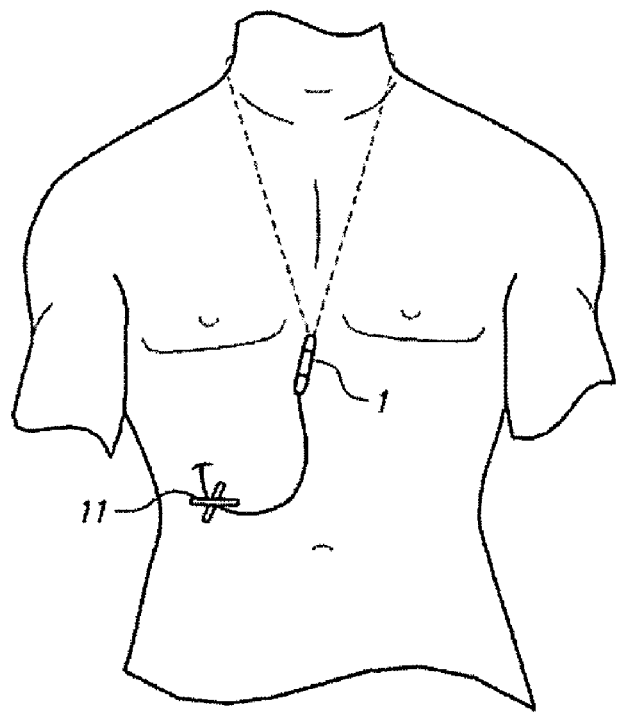
FIG. 3A shows the catheter 1 and housing with a necklace 7.
Figure 3C:
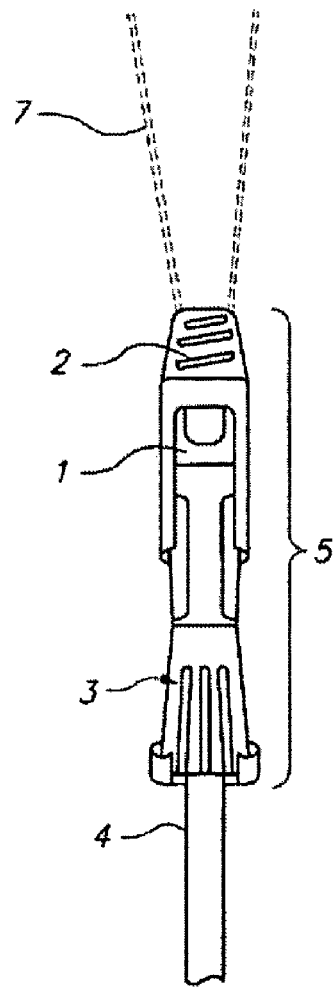
FIG. 3B shows the catheter housing.

FIG. 3C shows the catheter 1 in the housing 5 on a necklace 7.

Figure 4A:
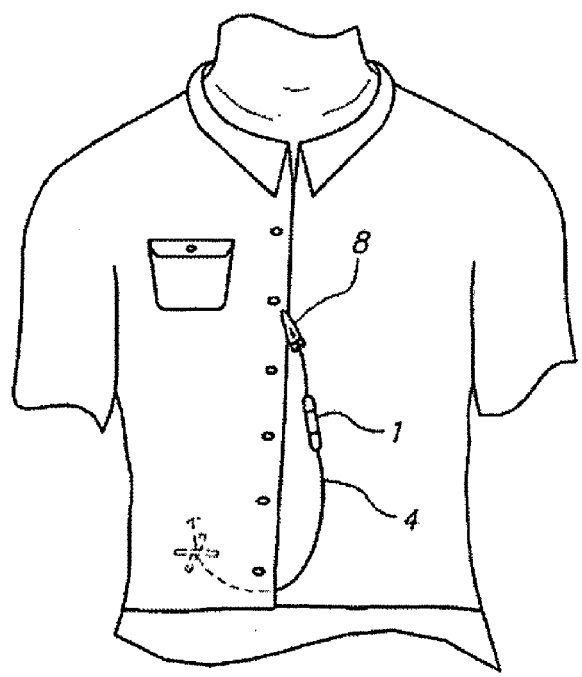

FIG. 4A shows the catheter 1 and housing with an alligator clip 8.

Figure 4C:
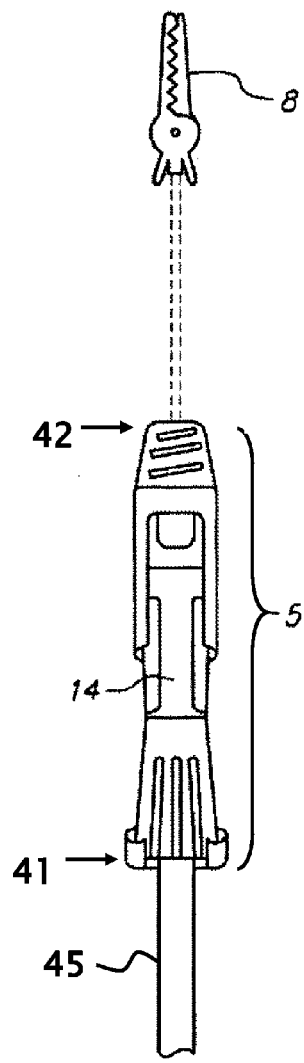
Figure 4B:
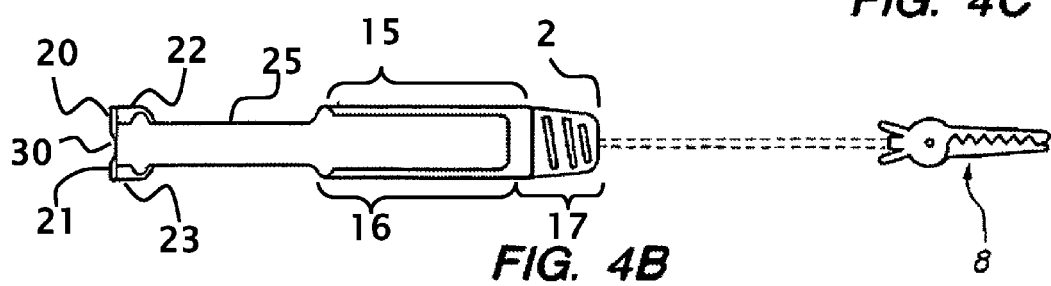

FIG. 4B shows the catheter housing 5 with the alligator clip 8.

FIG. 4C shows the catheter 1 in the housing 5 with the alligator clip 8.

Figure 5:
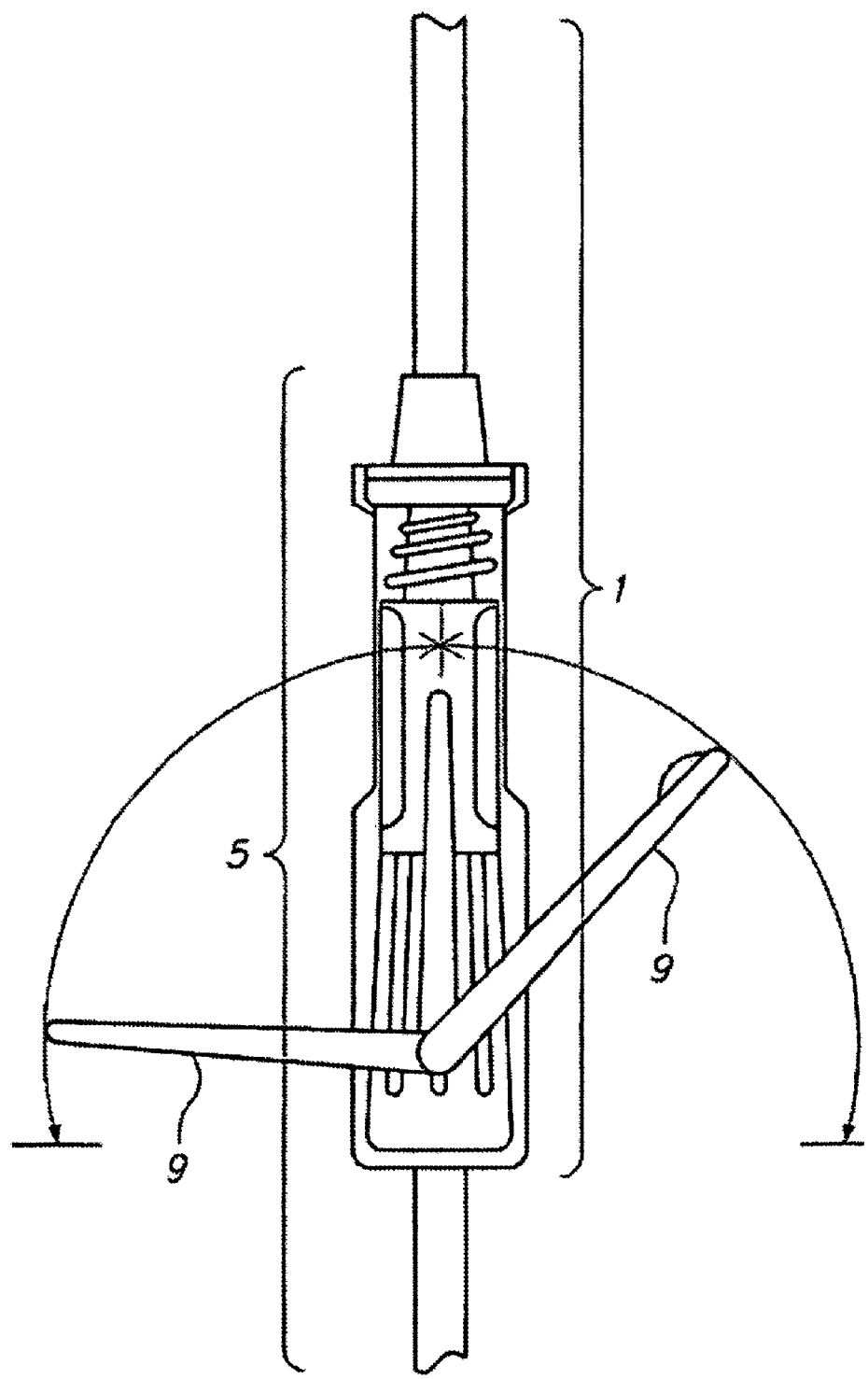

FIG. 5 shows the catheter 1 and housing 5 with a clip-on 9.

DETAILED DESCRIPTION OF THE INVENTION

Figure 1:
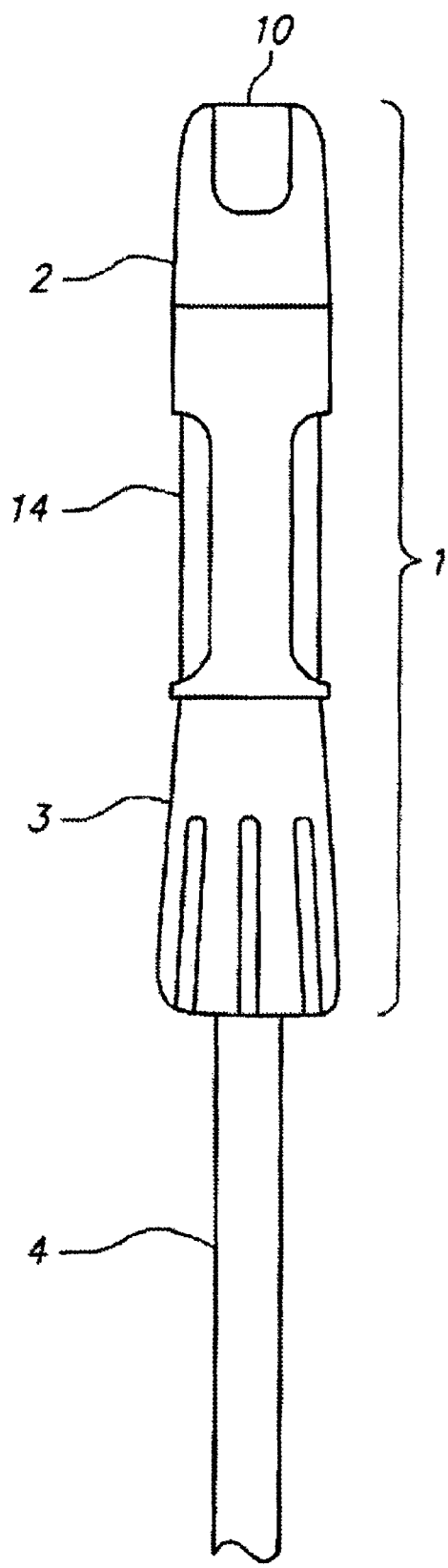

FIG. 1 illustrates the components of a catheter 1 without any housing. The catheter 1 consists of a connected-end rubber hose 10, a removable cap 2, a twist valve 3, and a free-end 4 of the rubber hose. The twist valve 3 secures the free-end of the hose 4. The removable cap 2 covers the opening for the connected-end of the rubber hose 10 that connects the catheter 1 to the body of the user at the Exit-Site 11.

FIG. 1 illustrates the catheter 1, the removable cap 2, the twist valve 3, and the rubber hose with a free-end 4 and a connected-end 10. In this figure the catheter 1 is shown retained within the proximal ends 41 and 42. The housing retains the catheter twist valve and the removable cap within the proximal ends 41 and 42 of the housing to prevent unintended disturbance of said twist valve or removable cap on the catheter 1. Each component of the retainer for a peritoneal dialysis catheter is shown as it is connected as a single unit, i.e.: the connected-end 10 catheter hose (leading to the body of the user); the removable cap 2; the twist valve 3, and the free-end 4 catheter. The middle portion 14 of the catheter valve holds the components together.

FIG. 2 shows the catheter 1 attached to the Exit-Site 11 in the user's abdomen. See FIG. 2C. The Catheter 1 is shown with the housing 5 in FIG. 2A. In FIG. 2A the housing 5 is shown with a clip connected 27 to the body of the housing 5. The clip has a slot with a tab 26 that helps to retain the housing 5 and the catheter 1 on a garment of clothing. The catheter hose 4 is shown attached to the Exit-Site 11 of the body of the user, with the free-end 4 connected to the dialysis machine 13 during treatment. An empty housing 5 is shown in FIG. 2B with the tab 26 extending along the housing 5 and being integrated 24 with the body of the housing 5.

Referring to FIG. 2, a catheter 1 is attached through the connected-end of the rubber hose 10 to the Exit-Site 11 of the patient, as shown. The word catheter generally refers to the rubber tubing of a medical device that is implanted in a patient's abdomen 12. The free-end of the catheter rubber hose 4 is attached to the dialysis solution container 13.

Referring to FIG. 3, my catheter housing 5 releasably connects all of the parts of the catheter 1 that are outside the patient's body, i.e. the twist valve 3, the removable cap 2, and the free-end of the catheter hose 4. The catheter housing 5 has a necklace 7 attachment means so that the catheter 1 may be attached around the neck of the user using the necklace 7, as illustrated.

Figure 3B:
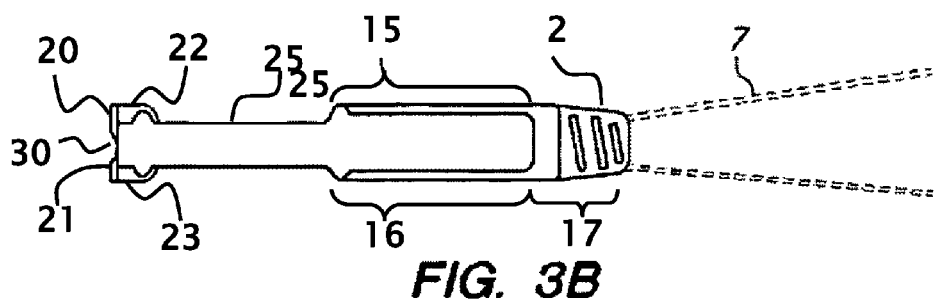

FIG. 3 shows a necklace 7 connected to the catheter housing 5. FIG. 3C. The necklace 7 is placed around the neck of the user, so that the catheter 1 in the housing 5 hangs free. The necklace 7 is shown connected to an empty housing in FIG. 3B. The housing 5 has a back supporting surface 25. The back support is flexible to bend around the catheter 1 when the catheter 1 in being installed and removed from the housing 5. On one end of the back supporting surface 25 a pair of side retainers 22 and 23 are joined with a pair of rear retainers 20 and 21 respectively. A clearance 30 exists between these two rear retainers 20 and 21 for the catheter hose 4 to pass between. The back support surface 25 also supports two front retainers 15 and 16 on opposing sides of the back support 25. These side retainers 15 and 16 provide side-to-side support of an installed catheter. The two front retainers 15 and 16 also support a pocket area 17 where the cap 2 covers the opening for the connected-end of the rubber hose 10 that connects the catheter 1 to the body of the user at the Exit-Site 11

During dialysis, the catheter 1 is connected to a dialysis machine by removing the cap and inserting the free-end 4 catheter hose into the dialysis machine 13. When the dialysis treatment is completed, the free-end 4 catheter hose is removed from the dialysis machine 13 and the removable cap 2 is placed again on the end of the free-end 4 catheter hose. The removable cap 2 remains and all other parts of the catheter 1 remain attached to the catheter housing 5 until the next treatment.

Referring to FIGS. 1 and 4C, the catheter valve has a middle-portion 14 to connect the removable cap 2 with the twist valve 3. The twist valve 3 accepts the free-end of the catheter hose 4 that comes from the dialysis machine 13.

In this figure the middle-portion 14 of the catheter is shown retained within the proximal ends 41 and 42. The housing 5 retains the catheter twist valve and the removable cap within the proximal ends 41 and 42 of the housing to prevent unintended disturbance of said twist valve or removable cap on the catheter. When not connected to the dialysis machine, the free-end of the catheter hose 4 must be secured to the body of the patient. See FIG. 3A.

The catheter housing 5 substitutes for the traditional means for securing the catheter components by tape or a belt with a necklace 7 or clip 9 that attaches the housing 5 containing the catheter to the body of the user. See. FIGS. 3C and 4C.

Referring to FIG. 4, in one preferred embodiment, my retainer for a peritoneal dialysis catheter utilizes a cylindrically-shaped catheter housing 5 (FIG. 48) to accept the combination of the removable cap 2, the middle-portion 14 of the catheter valve, and the twist-valve 3. When the removable cap 2, the middle-portion 14, and the twist-valve 3 are put together, they are then snapped into place into the catheter housing 5. FIG. 4C.

FIG. 4 shows an alligator clip 8 connected to the catheter 1 in the holder 5. FIG. 4C. The alligator clip 8 is shown connected to an empty housing in FIG. 4B. The housing 5 has a back supporting surface 25. On one end of the back supporting surface 25 a pair of side retainers 22 and 23 are joined with a pair of rear retainers 20 and 21 respectively that provide lateral support to an installed catheter. A clearance 30 exists between these two rear retainers 20 and 21 for the catheter hose 4 to pass between. The back support surface 25 also supports two front retainers 15 and 16 on opposing sides of the back support 25. The back support 25 is flexible to bend around the catheter 1 when the catheter 1 in being installed and removed from the housing 5. These side retainers 15 and 16 provide side-to-side support of an installed catheter. The two front retainers 15 and 16 also support a pocket area 17 where the cap 2 covers the opening for the connected-end of the rubber hose 10 that connects the catheter 1 to the body of the user at the Exit-Site 11. The alligator clip is attached to the clothing of the user, so that the catheter 1 and the housing 5 hang free while the connected-end of the hose 4 remains connected to the Exit-Site 11. See FIG. 4A.

The housing has an alligator clip 8 or similar attachment means, so that the catheter 1 may be easily attached to the clothing of the user. FIG. 4A.

In preferred embodiments, the attachment means is a clip 9 (FIG. 5) or necklace 7 (FIG. 3C) that easily and freely keeps the catheter housing 5 attached to the body of the user. The main object of my retainer for a peritoneal dialysis catheter is to provide a housing device to make it easier to hold together a catheter valve 14 and the removable cap 2, the twist-valve 3, and the free-end of the catheter hose 4 and the connected end of the catheter hose 10 while attaching the same to a human body or patient. FIGS. 1 and 2C.

FIG. 5 shows the housing 5 with a clip-on attachment 9. The clip is adjustable.

By holding the components of the catheter in a single housing unit 5, my retainer for a peritoneal dialysis catheter increases the freedom of movement of the user because the patient is unencumbered by any tape or belt. See FIGS. 3A and 4A.

The elimination of tape removes the risk of cuts and infection, while the lack of a belt or bulky pouch significantly increases the freedom of movement for the user while eliminating areas for collecting water and dirt. See FIGS. 3C, 4C, and 5.

It is an object of my catheter housing retainer for a peritoneal dialysis catheter to provide a holder for a peritoneal dialysis catheter which is safer and more comfortable than traditional methods for securing catheters between dialysis treatments. An additional object of my retainer for a peritoneal dialysis catheter is to increase the user's freedom of movement. It is a further object of my retainer for a peritoneal dialysis catheter to increase safety by reducing infections by allowing for the wearer to take a full shower.

It is a further object of the retainer for a peritoneal dialysis catheter to eliminate the need to shave the abdomen of the wearer and thereby eliminate the risks of nicking and cutting the tubes while shaving. My retainer for a peritoneal dialysis catheter also eliminates the need for taping the catheter to the body of the user.

My retainer for a peritoneal dialysis catheter also reduces maintenance between dialysis treatments by providing two holders, one for use when the catheter is connected to the dialysis machine (FIG. 2C) and another for use when disconnected (FIG. 3A).

My retainer for a peritoneal dialysis catheter achieves these objects by providing a catheter housing 5 for the free-end of the catheter hose and a means for securing the housing to the body of the user while holding together the components of the catheter in a single unit.

DETAILED DESCRIPTION OF THE DRAWINGS AND THE BEST MODE AND PREFERRED EMBODIMENTS OF THE RETAINER FOR A PERITONEAL DIALYSIS CATHETER

Prior to my retainer for a peritoneal dialysis catheter, the catheter device swung freely, unless taped to the body of the patient or secured by a belt. With the retainer for a peritoneal dialysis catheter's use of a means for securing to the body of the user, e.g. a necklace 7, clip-on 8 or similar attachment means, significant safety and comfort advantages accrue to the user. See FIGS. 3C and 4C.

Use of the catheter housing 5 eliminates the need for tape and the shaving necessary before taping and avoids skin irritation and rashes due to repetitive applications and removals of tape. Eliminating tape through use of the holder significantly increases the user's Freedom of movement. See FIGS. 3 and 4.

An alternative to taping is to hold the catheter device in a belt or similar piece of apparel. However, the bulkiness of the belt significantly reduces the mobility of the person wearing the belt. My retainer for a peritoneal dialysis catheter (foes not use nylon straps or cotton netting belts. See FIG. 2. As a result, the user's comfort is increased. Without belts and tape and the like, the wearer of the retainer for a peritoneal dialysis catheter may more easily take a shower and clean all parts of the body and abdomen. Without tape and belts, the patient is able to reduce the risk of infection because he is able to keep his body clean.

The parts of the retainer for a peritoneal dialysis catheter are as follows:

A catheter housing 5 for a catheter 1 and its parts, i.e. a twist valve 3, a middle-portion 14, a removable cap 2, and rubber hose with a free-end 4 and a connected-end 10. FIG. 1.

The rubber hose connects the catheter 1 to the dialysis machine 13. FIG. 2. The middle-portion 14 accepts the removable cap 2 on one end and the twist valve 3 on the other. The twist valve 3 connects the connected-end 10 of the hose leading to the Exit-Site in the body of the user 11. The removable cap 2 accepts a hose that connects the free-end of the hose 4 to the dialysis machine 13. See FIGS. 1 and 2.

The Exit-Site 11 is where the dialysis hose is surgically attached inside the patient. See FIG. 2C.

My catheter housing improves upon U.S. Pat. No. 4,578,062 because no belt or extra clothing is required to secure the catheter device to the body of the user. My catheter housing 5 improves upon U.S. Pat. No. 5,688,248 issued to Kennith C. Lessing, Jr. and U.S. Pat. No. 6,682,507 issued to Douglas H. Irish by eliminating the need for a belt.

My retainer for a peritoneal dialysis catheter improves upon the prior art of using garments to hold the catheter by eliminating the need for any clothing garment worn by the patient. See FIGS. 3A, 4A, and 5. See U.S. Pat. No. 6,206,854 issued on Mar. 27, 2001 to Kathleen M. Weaver titled Catheter Garment.

The following are the preferred embodiments of my retainer for a peritoneal dialysis catheter:

Mode One: The catheter housing 5 is clipped to waist and connected to the dialysis machine 13. FIG. 2C. The catheter housing 5 is shown separately in FIG. 2B.

Mode Two: The catheter housing 5 is attached to the body of the user with a necklace 7 or similar attachment means. See FIG. 3. The catheter housing with a necklace attachment means is shown in FIG. 3B.

In another version of Mode Two: The catheter housing 5 is attached to the body of the user with an alligator clip 8 or similar attachment means. See FIG. 4. The catheter housing with an alligator attachment means is shown in FIGS. 4B and 4C.

Mode Three: The catheter housing 5 also has a clip-on 9 mechanism which can be secured to the clothing of the patient. FIG. 5.

In a first embodiment of the retainer for a peritoneal dialysis catheter (Mode I), the necklace holder can be used daily. A smooth nylon string will connect to the plastic holder and will support the catheter valve safely and comfortably. See FIG. 3A. The empty catheter housing is attached to a necklace. FIGS. 3B and 3C.

In a second embodiment of the retainer for a peritoneal dialysis catheter (Mode II), an alligator clip 8 is used to attach the catheter 1 to a shirt or undergarment. See FIG. 4A.

In a third and preferred embodiment of the retainer for a peritoneal dialysis catheter (Mode III), the catheter housing 5 incorporates a clipping mechanism or clip-on 9 to attach the housing 5 to pajamas or underwear worn by the user. As shown in FIG. 5.

The features and advantages of the present retainer for a peritoneal dialysis catheter will be made clear from the following detailed description of the figures. My retainer for a peritoneal dialysis catheter is illustrated by way of non-limiting examples in the accompanying drawings.

Thus, specific embodiments of a user wearable device for carrying peritoneal dialysis catheter have been disclosed. It should be apparent, however, to those skilled in the art that many more modifications besides those described are possible without departing from the inventive concepts herein.

The inventive subject matter, therefore, is not to be restricted except in the spirit of the appended claims.

The invention claimed is:

1. A user wearable catheter carrying device comprising:
   a housing;
   a catheter twist valve that is temporally securable to said catheter;
   a removable cap that is temporarily securable to said catheter;
   a hose that is connected to a catheter comprising a free-end and a connected-end;
   said housing releasably connects said catheter twist valve and said removable cap within a pocket area of said housing;
   said catheter twist valve, said removable cap, and at least a portion of said hose are held together essentially longitudinally as a single unit inside said housing with two rear retainers having walls that partially surround said catheter twist valve and said hose passing through said housing between said two rear retainers;
   said removable cap is placed against a free end of said catheter hose within said housing where the catheter is temporally retained between said pocket area and said two rear retainers of said housing to prevent unintended disturbance of said twist valve or removable cap on said catheter;
   said hose extends freely out of a free end of said housing to an exit site, and
   a string or chain necklace, an alligator-clip on a string or a clip-on a string for suspended attachment of the catheter carrying device on a user.

2. The user wearable catheter carrying device of claim 1, wherein the housing is a cylindrically-shaped receptacle with a flexible back support that provides a means for flexing around said catheter for securely accepting the catheter, the catheter twist valve and the removable cap.

3. The user wearable catheter carrying device of claim 1, wherein said housing is made of plastic.

4. A method for securing the catheter device of claim 1 to the user, consisting of the steps of:
   (a) securing the catheter, catheter twist valve and removable cap together into a single unit by placing said removable cap into said free end of said housing;
   (b) rotating said catheter inside the housing and passing said hose between said two rear retainers, and
   (c) securing the housing to the user with a wearing means.

5. The method for securing a catheter device of claim 4, the method consisting of the steps of:
   a) forming the catheter, catheter twist valve and removable cap into a single unit;
   (b) placing the single unit into the housing, and
   (c) attaching the housing to the user with the necklace, an alligator-clip on a string or a clip-on a string.

6. The method for securing a catheter device of claim 5 to a user, wherein the catheter twist valve, the removable cap, and the hose are pressed together essentially longitudinally as a single hanging/suspended unit inside the housing and the housing is secured to the body of the user by the necklace, an alligator-clip on a string or a clip-on a string.

7. The user wearable catheter carrying device of claim 1, wherein the catheter carrying device is suspended at a location that is removed from an exit-site in the body of the user.

8. The user wearable catheter carrying device of claim 1, wherein one end of the housing has an opening whereby allowing said hose to exit said catheter carrying device between said pair of retainers.

9. The user wearable catheter carrying device of claim 1, wherein said housing has side walls for lateral support of said catheter.

10. The user wearable catheter carrying device of claim 1, wherein said side walls join at one end of said housing to create a closed pocket with at least one open elongated side, whereby said catheter is removable from said housing through said at least one open elongated side.

11. The user wearable catheter carrying device of claim 10, wherein said housing is flexible to bend around both elongated ends of said catheter when said catheter is being installed and removed from said housing.

12. The user wearable catheter carrying device of claim 1, wherein said closed pocket accepts said free end of said catheter.

13. The user wearable catheter carrying device of claim 1, wherein said housing further includes an integral clip.

14. The user wearable catheter carrying device of claim 13, wherein said integral clip is an elongated member that allows an article of clothing to pass between said elongate member and said housing.

* * * * *